(12) United States Patent
Pessel et al.

(10) Patent No.: US 11,224,220 B2
(45) Date of Patent: Jan. 18, 2022

(54) SURFACTANT COMPOSITION BASED ON GLYCINE BETAINE AMIDE SALTS, PROCESS FOR PREPARING SAME AND USES THEREOF

(71) Applicant: SURFACTGREEN, Compiegne (FR)

(72) Inventors: Freddy Pessel, Bedee (FR); Francis Galle, Rennes (FR); Pierre-Yves Divet, Neuilly sur Seine (FR); Xavier Roussel, Le Mans (FR)

(73) Assignee: SURFACTGREEN, Compiegne (FR)

( * ) Notice: Subject to any disclaimer, the term of this patent is extended or adjusted under 35 U.S.C. 154(b) by 2 days.

(21) Appl. No.: 16/445,441

(22) Filed: Jun. 19, 2019

(65) Prior Publication Data

US 2019/0380333 A1    Dec. 19, 2019

(30) Foreign Application Priority Data

Jun. 19, 2018   (FR) ...................................... 1855359

(51) Int. Cl.
| | | |
|---|---|---|
| *A01N 25/30* | (2006.01) | |
| *A61K 8/41* | (2006.01) | |
| *A61K 8/42* | (2006.01) | |
| *A61K 8/44* | (2006.01) | |
| *C11D 1/62* | (2006.01) | |
| *A61Q 19/10* | (2006.01) | |
| *C11D 1/645* | (2006.01) | |

(52) U.S. Cl.
CPC .............. *A01N 25/30* (2013.01); *A61K 8/416* (2013.01); *A61K 8/42* (2013.01); *A61K 8/44* (2013.01); *A61Q 19/10* (2013.01); *C11D 1/645* (2013.01); *A61K 2800/596* (2013.01); *C11D 1/62* (2013.01)

(58) Field of Classification Search
CPC combination set(s) only.
See application file for complete search history.

(56) References Cited

U.S. PATENT DOCUMENTS

| | | | |
|---|---|---|---|
| 7,829,521 B2 | 11/2010 | Antoine et al. | |
| 2007/0197420 A1 | 8/2007 | Antoine et al. | |
| 2010/0273694 A1 | 10/2010 | Antoine et al. | |
| 2013/0338227 A1* | 12/2013 | Saint Victor | C11D 3/222 514/551 |

FOREIGN PATENT DOCUMENTS

| | | |
|---|---|---|
| WO | WO 2005/121291 | 12/2005 |
| WO | WO 2013/188508 | 12/2013 |
| WO | WO 2017/034793 | 3/2017 |

OTHER PUBLICATIONS

Goursaud, F. "Glycine betaine as a renewable raw material to "greener" new cationic surfactants" *Green Chemistry*, 2008, pp. 310-320, vol. 10, No. 3.

* cited by examiner

*Primary Examiner* — Timothy P Thomas
(74) *Attorney, Agent, or Firm* — Saliwanchik, Lloyd & Eisenschenk

(57) ABSTRACT

The present invention relates to a surfactant composition based on glycine betaine amide salt and also to the process for preparing the same. The invention also relates to the use thereof as a wetting agent, particle dispersant and/or corrosion inhibitor and/or for improving the disinfectant power and/or the persistence of the disinfectant effect of antimicrobial substances and/or the insecticide effect and/or the persistence of insecticidal substances, and also in the manufacture of various products intended for treating and/or cleansing the body, plants or hard surfaces, for water treatment or for oil extraction. The invention also relates to a product comprising the abovementioned composition.

6 Claims, No Drawings

SURFACTANT COMPOSITION BASED ON GLYCINE BETAINE AMIDE SALTS, PROCESS FOR PREPARING SAME AND USES THEREOF

SUBJECT OF THE INVENTION

The present invention relates to a surfactant composition based on glycine betaine amide salts, and also to the process for preparing same. The invention also relates to the use thereof as a wetting agent, particle dispersant and/or corrosion inhibitor and/or for improving the disinfectant power of antimicrobial substances and/or the effect of insecticidal substances, and also in the manufacture of various products intended for treating and/or cleansing the body, plants or hard surfaces, for water treatment or oil extraction. A subject of the invention is also a product comprising the abovementioned composition.

BACKGROUND OF THE INVENTION

Surfactants constitute starting materials that are essential for the manufacture of a diversity of products. Among these, cationic surfactants represent, admittedly, a less broad market than that of anionic or nonionic surfactants, but they are nevertheless of interest in multiple applications, notably in the manufacture of detergent and cosmetic products, and also in water treatment.

On account of their toxicity, certain surfactants such as dimethyldialkylammonium salts, which are present in the majority of textile softeners, are becoming limited in use, or even abandoned, in certain European countries such as Germany and the Netherlands. Under ecological pressure, surfactant producers must propose products that are not only less pollutant but also more biodegradable and which have the smallest possible ecotoxicity. Added to the environmental constraints is the consumer desire for products that are as natural as possible.

In this context, glycine betaine, a relatively inexpensive natural substance, constitutes a starting material of choice for the preparation of surfactants. Derived from sugar beet molasses, obtained after sucrose extraction, it currently remains a byproduct of the sugar industry. Grafting fatty alcohols and amines onto glycine betaine affords access to cationic amphiphilic molecules without the conventional step of quaternization of a tertiary amine using generally toxic methylating agents.

U.S. Pat. No. 7,829,521 has thus proposed glycine betaine amides obtained by reacting glycine betaine with a sulfonic acid, such as methanesulfonic acid, and an alcohol, such as n-butanol, to produce a glycine betaine ester which is then subjected to an aminolysis reaction using a fatty amine of plant origin comprising at least 18 carbon atoms. The cationic surfactants thus obtained have a surface tension of at least 36 mN/m and are more particularly intended for cosmetic use. Other similar shorter-chain surfactants are presented in the publication from F. Goursaud et al. in *Green Chem.*, 2008, 10, 310-320, namely glycine betaine laurylamide, the surface tension of which is once again very high (50 mN/m). This surfactant is also described in patent application WO 2013/188508. In said document, it is demonstrated (Table 5) that the crude reaction mixture has a lower surface tension (25 mN/m) than pure glycine betaine amide (38 mN/m), making it possible to envisage its use in household detergents. This reaction mixture precisely contains 68% of laurylamide, 29% of laurylamine ammonium salts and 3% of residual glycine betaine.

By modifying the operating conditions described in WO 2013/188508, the inventors have been able to obtain a surfactant composition enriched in glycine betaine amide and depleted in alkylammonium salts, which was found to have a lower surface tension than the surfactant compositions described in said document and which is consequently suitable for many other applications.

A similar composition, based on a mixture of glycine betaine laurylamide and lauryl betaine myristylamide, was mentioned in WO 2017/034793. However, the very general process presented in said document does not make it possible to obtain this composition, a fortiori reproducibly, owing to a lack of indication regarding the precise operating parameters used.

The synthetic process used according to the invention is simple, efficient, environmentally friendly, solvent-free and, does not discharge pollutants and is readily transposable to the industrial scale to reproducibly obtain a particularly high-performance surfactant composition.

SUMMARY OF THE INVENTION

A subject of the invention is a surfactant composition comprising:

(a) from 70% to 85% by weight of one or more glycine betaine amide salts of formula (1): $X^{n-}[(CH_3)_3N^+—CH_2—CONH—R]_n$, in which R is a saturated or unsaturated linear alkyl group comprising from 8 to 18 carbon atoms, it being understood that 40% to 100% by weight of the salts of formula (I) consist of glycine betaine laurylamide salt;

(b) from 5% to 20% by weight of alkylammonium salt of formula (2): $X^{n-}[NH_3^+R]_n$ in which R is a saturated or unsaturated linear alkyl group comprising from 8 to 18 carbon atoms, it being understood that at least 40% by weight of the alkylammonium salts of formula (2) consist of laurylammonium salt;

(c) from 5% to 10% by weight of glycine betaine ester salt of formula (3): $X^{n-}[(CH_3)_3N^+—CH_2—COOR']_n$ in which R' is a linear or branched alkyl radical containing from 4 to 8 carbon atoms; and (d) from 0 to 5% by weight of glycine betaine of formula (4): $(CH_3)_3N^+—CH_2—COO^-$;

in which:
X is an organic or inorganic anion
and n is 1 or 2.

A subject of the invention is also a process for preparing this surfactant composition, comprising the successive steps consisting in:

(1) reacting glycine betaine or a salt thereof with a linear or branched $C_4$-$C_8$ alcohol, in the presence of an organic or inorganic acid, at a temperature of from 100 to 180° C. and under reduced pressure;

(2) cooling the reaction mixture to a temperature of from 20 to 80° C.;

(3) adding one or more alkylamines containing from 8 to 18 carbon atoms, including at least 40% by weight of laurylamine;

(4) removing the residual alcohol; and (5) recovering the surfactant composition thus obtained, characterized in that:

either step (1) is performed under conditions making it possible to achieve a degree of conversion of glycine betaine into glycine betaine ester salt of at least 95%, as measured by $^1$H NMR and defined by the following equation:

$$\eta = \frac{I_{XOGBOR'}/2}{I_{XOGB}/2 + I_{XOGBOR'}/2} = \frac{I_{XOGBOR'}}{I_{XOGB} + I_{XOGBOR'}}$$

in which:

η is the degree of conversion $I_i$ is the integration value of the characteristic signal of the compound i [(4.35 ppm, s, 2H) for XOGBOR', (4.28 ppm, s, 2H) for XOGB when X=mesylate]

XOGBOR' denotes the glycine betaine ester salt formed

XOGB denotes the glycine betaine salt formed, or the glycine betaine ester salt formed in step (1) is separated from the reaction mixture between steps (2) and (3) and reacted with the alkylamine(s) in step (4).

A subject of the invention is also the use of the abovementioned surfactant composition as a wetting agent, particle dispersant and/or corrosion inhibitor and/or for improving the disinfectant power and/or the persistence of the disinfectant effect of antimicrobial substances and/or for improving the effect and/or persistence of insecticidal substances.

A subject of the invention is also the use of this composition for the manufacture of plastics or of products intended:

for treating and/or cleansing the body, plants or hard surfaces, in particular cosmetic products, vehicle washing products, household products, industrial cleaning products, fibre sizing products and plant-protection products;

for water treatment;

for oil extraction.

A subject of the invention is also a product comprising the abovementioned composition and at least one constituent chosen from: (a) anionic surfactants, nonionic surfactants and mixtures thereof and/or (b) antimicrobial agents and/or insecticidal substances.

Besides its low surface tension, the surfactant composition according to the invention has the advantage of being biodegradable (according to the standard OECD 310), sparingly toxic to the environment (according to the standards OECD 201 and 202) and to humans, cold-soluble, stable irrespective of the pH and of having good foaming power.

DETAILED DESCRIPTION

Surfactant Composition

The surfactant composition according to the invention comprises:

(a) from 70% to 85% by weight of one or more glycine betaine amide salts of formula (1): $X^{n-}[(CH_3)_3N^+\text{—}CH_2\text{—}CONH\text{—}R]_n$, in which R is a saturated or unsaturated linear alkyl group comprising from 8 to 18 carbon atoms, it being understood that 40% to 100% by weight of the salts of formula (I) consist of glycine betaine laurylamide salt;

(b) from 5% to 20% by weight of alkylammonium salt of formula (2): $X^{n-}[NH_3^+R]_n$, in which R is a saturated or unsaturated linear alkyl group comprising from 8 to 18 carbon atoms, it being understood that at least 40% by weight of the alkylammonium salts of formula (2) consist of laurylammonium salt;

(c) from 5% to 10% by weight of glycine betaine ester salt of formula (3): $X^{n-}[(CH_3)_3N^+\text{—}CH_2\text{—}COOR']_n$ in which R' is a linear or branched alkyl radical containing from 4 to 8 carbon atoms; and (d) from 0 to 5% by weight of glycine betaine of formula (4): $(CH_3)_3N^+\text{—}CH_2\text{—}COO^-$;

in which:

X is an organic or inorganic anion and n is 1 or 2.

The group X may notably be chosen from anions derived from organic or inorganic acids. It may in particular be a chloride, a sulfate, a perchlorate, an alkyl sulfate ion, notably decyl sulfate or lauryl sulfate, an arylsulfonate ion, notably benzenesulfonate, para-toluenesulfonate, camphorsulfonate, an alkylsulfonate ion, notably triflate, methanesulfonate, ethanesulfonate, decylsulfonate, laurylsulfonate, a sulfosuccinate ion, and mixtures thereof. It is preferred according to the invention for X to be chosen from alkylsulfonates and arylsulfonates, in particular from methanesulfonate, ethanesulfonate, triflate, para-toluenesulfonate and camphorsulfonate ions. It is advantageously the methanesulfonate ion.

It is moreover preferred for R' to denote the butyl radical, notably n-butyl.

Advantageously, the compounds of formulae (1), (2), (3) and (4) represent in total from 90% to 100% and preferably from 95% to 100% of the weight of the composition. Better still, the composition according to the invention exclusively comprises the compounds of formulae (1), (2), (3) and (4).

Process

The surfactant composition according to the invention may be prepared according to a process as described previously.

The first step of this process consists of an esterification reaction of glycine betaine, or trimethylglycine. Glycine betaine may be of plant origin or synthetic origin. It may optionally be in salt form, for example inorganic salt form. It is generally necessary to protonate it beforehand using an organic or inorganic acid, in so far as it is in zwitterionic form (presence of a carboxylate function), except in the case where a glycine betaine salt is used. The acid may notably be chosen from inorganic acids such as hydrochloric acid, sulfuric acid, perhalohydric acids, such as perchloric acid, and mixtures thereof. As a variant, it may be chosen from organic acids, such as alkylsulfuric acids, for example decylsulfuric or laurylsulfuric acid; arylsulfonic acids, such as benzenesulfonic acid, para-toluenesulfonic acid, camphorsulfonic acid; alkylsulfonic acids, such as triflic acid, methanesulfonic acid, ethanesulfonic acid, decylsulfonic acid, laurylsulfonic acid; sulfosuccinic acid; and mixtures thereof. Lewis acids may also be used. Preferably, it is an alkysulfonic acid and in particular methanesulfonic acid.

During the actual esterification, the betaine acid reacts with the linear or branched $C_4$-$C_8$ alcohol in the presence of the acid to give a glycine betaine ester in salt form. Examples of alcohols comprise butanol, pentanol, 3-methylbutan-1-ol (or isoamyl alcohol), fusel alcohol (mixture of pentanol, 2-methylbutan-1-ol and 3-methylbutan-1-ol), hexanol, heptanol, octanol and mixtures thereof. The term "butanol" refers equally in this description to n-butanol, isobutanol and sec-butanol. Butanol, and more particularly n-butanol, is preferred for use in this invention. This reaction is generally performed in the absence of any solvent, the alcohol used constituting both the reagent and the medium. The water produced during the reaction also contributes towards dissolving the glycine betaine in the reaction mixture.

For the implementation of this step, use may be made of from 1.1 to 20 equivalents, for example from 2 to 4 equivalents, of linear or branched $C_4$-$C_8$ alcohol and from 1.0 to 1.5 equivalents of sulfonic acid, for example from 1.0 to 1.2 equivalents and preferentially 1.1 equivalents of sulfonic acid, per 1 equivalent of glycine betaine. The esterification may be performed at a temperature of from 100 to 180° C., preferentially from 100 to 160° C., more preferentially from 120 to 150° C. or from 130 to 160° C. at atmospheric pressure or under reduced pressure. During this reaction, the equilibrium is shifted towards the formation of the reaction product by distillation of the water-alcohol mixture, typically using Dean-Stark apparatus.

In a first variant of the invention, the esterification conditions are adjusted to achieve a degree of conversion of at least 95%. To do this, the reaction medium is placed under reduced pressure, if it is not already. The pressure will generally be proportionately lower the longer the chain of the fatty alcohol involved. A person skilled in the art will in any case be able to adjust the chosen pressure so as to remove the water formed during the reaction and to shift the equilibrium towards the formation of the ester. Similarly, the reaction time will be adjusted as a function of the alcohol used. In the case of butanol, the distillation may be started, for example, after 2 to 4 hours of reaction time and continued for 2 to 4 hours before lowering the pressure, for example to a value of from 500 to 900 mbar, notably from 600 to 800 mbar.

In contrast with the known processes for synthesizing glycine betaine amides, the degree of conversion of glycine betaine into glycine betaine ester sulfonate salt is monitored by $^1$H NMR and the reaction is continued until it reaches a value of at least 95%, i.e. for a time ranging, for example, from 5 to 48 hours.

Once this step is complete, and in contrast with the prior art processes, it is not useful to add to the reaction medium a strong, hindered organic base, such as dibutylamine.

The reaction medium is then cooled to a temperature of from 20 to 80° C., preferably from 40 to 80° C. in the first variant described above.

In a second variant of the process according to the invention, it is not necessary for the degree of conversion of the glycine betaine to be at least 95% and it may be from only 75% to 90%, for example about 80%, before the abovementioned cooling step, which will be performed in this case preferably down to a value of from 20 to 40° C. In this second variant, the product of the esterification reaction is, however, treated so as to separate the glycine betaine ester salt formed from the reaction medium. To do this, filtration of the reaction medium may be performed, for example, which makes it possible to separate out the abovementioned salified ester, which is soluble in the alcohol, from the other constituents which are not soluble.

One or more C8-C16 alkylamines including at least 40% by weight of laurylamine are then added either to the reaction medium (first variant) or to the isolated ester (second variant). To do this, use may be made either of laurylamine alone, or a mixture of laurylamine with other alkylamines obtained, for example, from coconut oil. Such a mixture typically contains from 40% to 60% by weight of laurylamine, from 15% to 22% by weight of myristylamine, from 5% to 12% by weight of palmitylamine, from 2% to 12% by weight of stearylamine, from 4% to 7% by weight of caprylamine and from 3% to 7% by weight of caprylylamine. The addition of alkylamine(s) is preferably performed after having removed a portion of the residual alcohol and the residual traces of water by distillation under reduced pressure. In this step, the alkylamine is advantageously used in molten form. The amount of alkylamine(s) added may represent, for example, from 0.9 to 1.5 equivalents and preferably from 1.0 to 1.2 equivalents per 1 equivalent of glycine betaine initially used. This aminolysis reaction is typically performed at a temperature of from 50 to 180° C. and preferably from 120 to 140° C., under reduced pressure, for example at a pressure of from 1 to 30 mbar.

In parallel to the aminolysis reaction, the alcohol is removed by distillation under reduced pressure. The aminolysis reaction and the distillation take place for a time of from 1 to 7 hours, notably from 3 to 5 hours.

The surfactant composition thus obtained is then recovered.

Uses

The surfactant composition according to the invention has a surface tension value of less than 24 mN/m, or even less than 22 mN/m and generally greater than or equal to 20 mN/m, measured according to the standard NF EN 14370.

It is thus possible to envisage its use in a diversity of applications such as wetting agent, particle dispersant and/or corrosion inhibitor and/or for improving the disinfectant power of antimicrobial substances and/or the effect of insecticidal substances. It may in particular be used for the manufacture of plastics or of various products intended notably:

for treating and/or cleansing the body, plants, textiles or hard surfaces, in particular cosmetic products, such as shampoos, liquid soaps, bubble baths and shower gels; products for washing vehicles such as motor vehicles, trucks, trains, buses or aeroplanes; household products such as detergents for glazings, wall surfaces, floors or kitchenware; laundry washing products or softeners; industrial cleaning products; fibre sizing products; plant-protection products; pigmented products such as paints or varnishes;

for water treatment;

for oil extraction.

When it is used in the cleaning of hard surfaces, such as glazings or vehicle bodywork surfaces, or textiles, it has been observed in particular that the composition according to the invention accelerates the subsequent drying of the surface without leaving traces of limescale on drying. In addition, when the surface is a vehicle, it has been observed that the cleaning of the fine braking particles on the wheels was improved when compared with conventional cationic surfactants. Finally, the efficiency of the composition according to the invention in alkaline medium makes it possible to avoid the drawbacks associated with the use of acidic compositions, in particular their corrosive effect.

In the case of water treatment, the composition according to the invention allows the detachment of biofilm without destroying the efficacy of the ion-exchange resins, in contrast with conventional cationic surfactants which moreover have an appreciable environmental impact given their absence of biodegradability, or their slower biodegradability. This capacity to detach biofilms may also be exploited in oil extraction processes.

In cosmetic applications, the composition according to the invention is compatible with conventional anionic surfactants and makes it possible to improve the creamy nature of the foam they generate. It also protects iron-containing aerosol devices against corrosion.

In the manufacture of plastics, the composition according to the invention makes it possible to impart electrostatic properties to the surface of the plastic, without affecting its recycling capacities, given its biobased nature.

When it is used in the manufacture of plant-protection products, the composition according to the invention makes it possible to improve the persistence of active materials and the water resistance of products such as herbicides, pesticides or plant growth modifiers, which may thus be used in smaller amount. This composition may thus be added, in a form diluted to 25% in water, at a rate of 0.4% by weight, in a product containing a neutral or alkaline medium, for example.

The composition according to the invention may moreover be used in a process for extracting, stockpiling, storing or refining oil to limit the corrosion of equipment. In this application, it may be added to oil in a proportion of from 500 to 1000 ppm, for example.

A subject of the invention is also a product chosen, for example, from those described above, comprising a composition according to the invention and at least one compound chosen from: anionic surfactants, nonionic surfactants, antimicrobial agents and/or insecticidal substances, and mixtures thereof. Examples of anionic surfactants are: ethoxylated fatty alcohol sulfate salts, sulfosuccinates, sarcosinates, alkyl and dialkyl phosphates, fatty acid soaps, and mixtures thereof. The nonionic surfactants may be chosen, for example, from: fatty acid esters of polyols such as optionally polyethoxylated fatty acid esters of glycerol, optionally polyethoxylated fatty acid esters of sorbitan, polyoxyethylene fatty acid esters, fatty acid esters of sucrose, for instance sucrose stearate; polyoxyethylene fatty alcohol ethers, fatty alcohol ethers of sugars, notably alkylpolyglucosides (APG), polysiloxane-modified polyethers, and mixtures thereof. The antimicrobial agents may be chosen from quaternary ammoniums, aldehydes (such as glutaraldehyde and formaldehyde), ethanol, halogenated derivatives, oxidizing agents, phenolic compounds, parabens, isothiazolones (or isothiazolinones), benzoates, imidazoline, hydantoin, guanidine, organic acids such as lactic acid, and mixtures thereof. The insecticidal substances may be chosen from organophosphorus agents (such as acephate, chlorpyrifos or bromophos), nicotinoids, pyrethroids (such as permethrin, bifenthrin or fenvalerate), monoterpenes (such as p-menthane-3,8-diol), organohalogen compounds (such as lindane, dicofol or toxaphene), N,N-diethyl-3-methylbenzamide, pyrethrum derivatives (such as pyrethrin I, pyrethrin II or jasmolin I), sulfones, sulfonates, formamidines, benzoylureas, rotenones, alkaloids, quassin, ryanidone, aconitin, geraniol, and mixtures thereof.

This product is advantageously in the form of an aqueous solution or an aqueous gel. As a variant, it may be in the form of an oil-in-water or water-in-oil emulsion or even a paste. In any case, the aqueous phase contained in this product advantageously has a pH ranging from 1 to 12, notably 8 to 12 and preferably from 9 to 11. This product may be packaged in any device suitable for the intended use and notably in a pump-action bottle, a tube, a jar, an aerosol device or a wipe.

It advantageously contains from 0.1% to 25% by weight, for example from 1% to 10% by weight, of surfactant composition according to the invention.

The product according to the invention may also comprise, in addition to the antimicrobial agents, insecticidal substances and surfactants mentioned previously, and depending on the intended application, at least one ingredient chosen from: plant-protection or cosmetic active agents, enzymes, chelating agents, thickeners, fatty substances (oils, waxes and/or pasty substances), fillers, preserving agents, pigments and dyes, antioxidants, optical brighteners, and mixtures thereof.

EXAMPLES

The invention will be understood more clearly in the light of the following examples, which are given for purely illustrative purposes and are not intended to limit the scope of the invention, defined by the attached claims.

Example 1: Synthesis of a Surfactant Composition According to the Invention (First Variant)

Glycine betaine (1.0 eq), butanol (3.0 eq) and 70% methanesulfonic acid solution (1.1 eq) are placed in a reactor on which is mounted a condenser. The mixture is heated to 140° C. at atmospheric pressure. After 3 hours of reaction, Dean-Stark equipment filled with butanol is mounted on the reactor. The mixture is left at atmospheric pressure since the distillation of the water-butanol azeotrope is sufficiently pronounced at the start. After a further 3 hours of reaction, when the distillation rate of the water-butanol azeotrope has decreased, the pressure is reduced to 700 mbar in order to accelerate the removal of the water and to enable the equilibrium to be shifted towards the glycine betaine butyl ester. The degree of conversion is monitored by $^1$H NMR analyses.

The NMR method consists in acquiring a $^1$H spectrum of the sample dissolved in a $CDCl_3/CD_3OD$ mixture (1/1, v/v), taking the methanol signal at 3.31 ppm as reference. The characteristic signals of the various compounds are then integrated: MsOGBOBu (4.35 ppm, s, 2H), MsOGB (4.28 ppm, s, 2H), butanol (3.53 ppm, t, 2H), methanesulfonate (2.74 ppm, s, 3H), dibutyl ether (3.40 ppm, t, 4H), where XOGBOBu denotes the glycine betaine ester sulfonate salt formed and XOGB denotes the glycine betaine sulfonate formed. The characteristic signal of the methanesulfonate takes into account both the methanesulfonic acid present in the medium, but also methanesulfonate which is the counterion of glycine betaine and of butyl betainate mesylate (MsOGBOBu).

The degree of conversion of the reaction is obtained by means of the integration values via the following calculation:

$$\eta = \frac{I_{MsOGBOBu}/2}{I_{MsOGB}/2 + I_{MsOGBOBu}/2} = \frac{I_{MsOGBOBu}}{I_{MsOGB} + I_{MsOBGOBU}}$$

in which:

η is the degree of conversion $I_i$ is the integration value of the characteristic signal of the compound i.

Once the degree of conversion of the esterification reaction reaches 98%, the reaction mixture is allowed to cool to 60° C. During this cooling phase, the Dean-Stark assembly is replaced with distillation apparatus and the reactor is placed under reduced pressure so as to remove a portion of the butanol and the remaining traces of water in the reaction mixture. Once the mixture is at 60° C., laurylamine (1.1 eq) which has been melted beforehand is added. The reaction mixture is then heated to 130° C. under reduced pressure. The pressure is gradually reduced to 10 mbar. After total distillation of the butanol (about 4 hours), the reaction mixture is recovered and constitutes the surfactant composition.

This composition has the following mass composition:

| Constituent | Molar mass (g/mol) | Weight % |
|---|---|---|
| Betainylaminododecane mesylate | 380.588 | 77% |
| Dodecylammonium mesylate | 281.455 | 15% |
| Butyl mesylate betainate | 269.356 | 7% |
| Glycine betaine | 117.148 | 1% |
| Butanol | 74.120 | 0% |

The surface tension of this surfactant composition was measured at the CMC, after adjusting the pH to 10 using sodium hydroxide.

The measurement of the surface tension was performed according to the standard NF EN 14370, using a Krüss tensiometer with a horizontally suspended platinum ring. Before each measurement, the ring is meticulously cleaned and flame-dried. The sample goblet is a conical PTFE container placed in a chamber thermally regulated at 25° C. The sample is prepared with Milli-Q water and stirred continually using a magnetic bar before each measurement.

The surface tension thus measured was 22 mN/m.

Example 2: Synthesis of a Surfactant Composition According to the Invention (Second Variant)

Glycine betaine (1.0 eq) and butanol (3.0 eq) are placed in a reactor on which is mounted Dean-Stark apparatus filled with butanol. The mixture is heated to 140° C. under a reduced pressure of 700 mbar. Once the nominal temperature and pressure values have been reached, 70% methanesulfonic acid solution is added to the mixture. The degree of conversion is monitored by $^1$H NMR analyses. Once the degree of conversion of the esterification reaction has reached about 80%, the reaction mixture is allowed to return to room temperature and atmospheric pressure. The mixture is then filtered so as to separate the solid glycine betaine mesylate from the butyl mesylate betainate which is dissolved in the butanol. The filtrate is introduced into a reactor on which is mounted distillation apparatus. Laurylamine (0.9-1.5 eq) which has been melted beforehand is added. The reaction mixture is then heated to 130° C. under reduced pressure. The pressure is gradually reduced to 10 mbar. After total distillation of the butanol (about 4 hours), the reaction mixture is recovered and constitutes the surfactant composition according to the invention.

Example 3: Synthesis of a Comparative Surfactant Composition

A surfactant composition was prepared in a manner similar to that of the process described in Example 1, except that the esterification conditions were adjusted so as to obtain a degree of conversion of only 91%.

To do this, glycine betaine (1.0 eq), butanol (3.0 eq) and 70% methanesulfonic acid solution (1.1 eq) are placed in a reactor on which is mounted Dean-Stark apparatus filled with butanol. The mixture is heated to 140° C. at atmospheric pressure. Despite a prolonged reaction time, the degree of conversion does not exceed 91%.

The reaction mixture is allowed to cool to 60° C. Once the mixture is at 60° C., laurylamine (1.1 eq) which has been melted beforehand is added. The reaction mixture is then heated to 130° C. under reduced pressure. The pressure is gradually reduced to 10 mbar. After total distillation of the butanol (about 4 hours), the reaction mixture is recovered and constitutes the surfactant composition.

The mass composition of the surfactant thus obtained is as follows:

| Constituent | Molar mass (g/mol) | Weight % |
|---|---|---|
| Betainylaminododecane mesylate | 380.588 | 68% |
| Dodecylammonium mesylate | 281.455 | 23% |
| Butyl mesylate betainate | 269.356 | 6% |
| Glycine betaine | 117.148 | 3% |
| Butanol | 74.120 | 0% |

This composition thus contains less glycine betaine laurylamide and more laurylammonium salt than the composition according to the invention. This difference has a direct impact on the surface tension of this composition, which proves to be higher than that of the surfactant composition according to the invention (25 mN/m at the CMC).

Example 4: Synthesis of a Surfactant Composition According to the Invention

Glycine betaine (1.0 eq) and hexanol (3.0 eq) are placed in a reactor on which is mounted Dean-Stark apparatus filled with hexanol. A pressure-equalized dropping funnel containing 70% methanesulfonic acid solution (1.1 eq) is mounted on the lid of the reactor. The mixture is stirred and heated to 160° C. under reduced pressure at 650 mbar. Once the reaction conditions have been reached, the 70% methanesulfonic acid solution is gradually added to the reaction mixture. Once the addition is complete, the pressure is uniformly reduced down to 350 mbar in order to accelerate the removal of water and to enable the equilibrium to be shifted towards the glycine betaine ester. The degree of conversion is monitored by $^1$H NMR analyses.

The NMR method consists in acquiring a $^1$H spectrum of the sample dissolved in a $CDCl_3/CD_3OD$ mixture (1/1, v/v), taking the signal of methanol at 3.31 ppm as reference. The characteristic signals of the various compounds are then integrated: MsOGBOC6 (4.35 ppm, s, 2H), MsOGB (4.28 ppm, s, 2H), hexanol (3.53 ppm, t, 2H), methanesulfonate (2.74 ppm, s, 3H), dihexyl ether (3.40 ppm, t, 4H), where XOGBOC6 denotes the glycine betaine ester sulfonate salt formed and XOGB denotes the glycine betaine sulfonate formed. The characteristic signal of the methanesulfonate takes into account both the methanesulfonic acid present in the medium, but also the methanesulfonate which is the counterion of the glycine betaine and of the hexyl mesylate betainate (MsOGBOC6).

The degree of conversion of the reaction is obtained by means of the integration values via the following calculation:

$$\eta = \frac{I_{MsOGBOC6}/2}{I_{MsOGB}/2 + I_{MsOGBOC6}/2} = \frac{I_{MsOGBOC6}}{I_{MsOGB} + I_{MsOGBOC6}}$$

in which:

$\eta$ is the degree of conversion $I_i$ is the integration value of the characteristic signal of compound i.

Once the degree of conversion of the esterification reaction has reached 98%, the reaction mixture is allowed to cool to 60° C. During this cooling phase, the Dean-Stark apparatus is replaced with distillation apparatus and the reactor is placed under reduced pressure so as to remove a portion of the hexanol and the remaining traces of water in the reaction mixture. Once the mixture is at 60° C., laurylamine (1.1 eq) which has been melted beforehand is added. The reaction mixture is then heated to 150° C. under reduced pressure. The pressure is gradually reduced to 10 mbar. After total distillation of the hexanol (about 4 hours), the reaction mixture is recovered and constitutes the surfactant composition.

This composition has the following mass composition:

| Constituent | Molar mass (g/mol) | Weight % |
|---|---|---|
| Betainylaminododecane mesylate | 380.588 | 76% |
| Dodecylammonium mesylate | 281.455 | 14% |
| Hexyl mesylate betainate | 297.41 | 9% |
| Glycine betaine | 117.148 | 1% |
| Hexanol | 102.177 | 0% |

The surface tension of this surfactant composition was measured at the CMC, after adjusting the pH to 10 with sodium hydroxide.

The measurement of the surface tension was performed according to the standard NF EN 14370, using a Krüss tensiometer with a horizontally suspended platinum ring. Before each measurement, the ring is meticulously cleaned and flame-dried. The sample goblet is a conical PTFE container placed in a chamber thermally regulated at 25° C. The sample is prepared with Milli-Q water and stirred continuously using a magnetic bar before each measurement.

The surface tension thus measured was 20 mN/m.

Example 5: Synthesis of a Surfactant Composition According to the Invention

Glycine betaine (1.0 eq) and octanol (3.0 eq) are placed in a reactor on which is mounted Dean-Stark apparatus filled with octanol. A pressure-equalized dropping funnel containing 70% methanesulfonic acid solution (1.1 eq) is mounted on the lid of the reactor. The mixture is stirred and heated to 160° C. under reduced pressure at 650 mbar. Once the reaction conditions have been reached, the 70% methanesulfonic acid solution is gradually added to the reaction mixture. Once the addition is complete, the pressure is uniformly reduced to 100 mbar in order to accelerate the removal of water and to enable the equilibrium to be shifted towards the glycine betaine ester. The degree of conversion is monitored by $^1$H NMR analyses.

The NMR method consists in acquiring a $^1$H NMR spectrum of the sample dissolved in a CDCl$_3$/CD$_3$OD mixture (1/1, v/v), taking the signal of methanol at 3.31 ppm as reference. The characteristic signals of the various compounds are then integrated: MsOGBOC8 (4.35 ppm, s, 2H), MsOGB (4.28 ppm, s, 2H), octanol (3.53 ppm, t, 2H), methanesulfonate (2.74 ppm, s, 3H), dioctyl ether (3.40 ppm, t, 4H), in which XOGBOC8 denotes the glycine betaine ester sulfonate salt formed and XOGB denotes the glycine betaine sulfonate formed. The characteristic signal of methanesulfonate takes into account both the methanesulfonic acid present in the medium, but also the methanesulfonate which is the counterion of the glycine betaine and the octyl mesylate betainate (MsOGBOC8).

The degree of conversion of the reaction is obtained by means of the integration values via the following calculation:

$$\eta = \frac{I_{MsOGBOC8}/2}{I_{MsOGB}/2 + I_{MsOGBOC8}/2} = \frac{I_{MsOGBOC8}}{I_{MsOGB} + I_{MsOGBOC8}}$$

in which:
$\eta$ is the degree of conversion
$I_i$ is the integration value of the characteristic signal of the compound i.

Once the degree of conversion of the esterification reaction has reached 99%, the reaction mixture is allowed to cool to 60° C. During this cooling phase, the Dean-Stark apparatus is replaced with distillation apparatus and the reactor is placed under reduced pressure so as to remove a portion of the octanol and the remaining traces of water in the reaction mixture. Once the mixture is at 60° C., laurylamine (1.1 eq) which has been melted beforehand is added. The reaction mixture is then heated to 150° C. under reduced pressure. The pressure is gradually reduced to 5 mbar. After total distillation of the octanol (about 4 hours), the reaction mixture is recovered and constitutes the surfactant composition.

This composition has the following mass composition:

| Constituent | Molar mass (g/mol) | Weight % |
|---|---|---|
| Betainylaminododecane mesylate | 380.588 | 75% |
| Dodecylammonium mesylate | 281.455 | 13% |
| Octyl mesylate betainate | 297.41 | 10% |
| Glycine betaine | 117.148 | 1% |
| Octanol | 102.177 | 1% |

The surface tension of this surfactant composition was measured at the CMC, after adjusting the pH to 10 with sodium hydroxide.

The measurement of the surface tension was performed according to the standard NF EN 14370, using a Krüss tensiometer with a horizontally suspended platinum ring. Before each measurement, the ring is meticulously cleaned and flame-dried. The sample goblet is a conical PTFE container placed in a chamber thermally regulated at 25° C. The sample is prepared with Milli-Q water and stirred continuously using a magnetic bar before each measurement.

The surface tension thus measured was 20 mN/m.

Example 6: Formulations

Several types of products may be prepared using the surfactant composition according to the invention, denoted hereinbelow "GBA C12".

| Household detergent | |
|---|---|
| 80% lactic acid | 2.00% |
| GBA C12 | 0.40% |

| Household detergent | |
| --- | --- |
| Hydroxyethylcellulose | 0.30% |
| Chelating agent | 0.20% |
| Fragrance | 0.20% |
| Dye | 0.01% |
| Deionized water | qs 100.00% |

This product may be used for cleaning hard surfaces.

| Vehicle bodywork shampoo | |
| --- | --- |
| GBA C12 | 3-5% |
| Ethoxylated alcohol | 0-5% |
| Chelating agent* | 5-10% |
| Sodium hydroxide | 0.5-2% |
| Water | qs 100% |

*Dissolvine ® GL from AkzoNobel or Trilon ® M from BASF

This product may be applied to a vehicle and then, after a leave-on time of 5 minutes, may be rinsed off at high pressure.

| Water treatment | |
| --- | --- |
| MEA (monoethanolamine) | 5-10% |
| GBA C12 | 20-25% |
| Antiredeposition polymer | 10-25% |
| Water | qs 100% |
| Insecticide | |
| Pyrethrum | 2% |
| Solubilizing agent | 3% |
| Sorbitan ester | 2% |
| GBA C12 | 1% |
| Pheromone | 0.2% |
| Antifoam | 0.1% |
| Water | qs 100% |

We claim:

1. A surfactant composition comprising:
    (a) from 70% to 85% by weight of one or more glycine betaine amide salts of formula (1): $X^{n-}[(CH_3)_3N^+—CH_2—CONH—R]_n$, in which R is a saturated or unsaturated linear alkyl group comprising from 8 to 18 carbon atoms, provided that 40% to 100% by weight of the salts of formula (I) are a glycine betaine laurylamide salt;
    (b) from 5% to 20% by weight of alkylammonium salt of formula (2): $X^{n-}[NH_3^+R]$ in which R is a saturated or unsaturated linear alkyl group comprising from 8 to 18 carbon atoms, provided that at least 40% by weight of the alkylammonium salts of formula (2) are a laurylammonium salt;
    (c) from 5% to 10% by weight of glycine betaine ester salt of formula (3): $X^{n-}[(CH_3)_3N^+—CH_2—COOR']n$ in which R' is a linear or branched alkyl radical containing from 4 to 8 carbon atoms; and
    (d) from 0 to 5% by weight of glycine betaine of formula (4): $(CH_3)_3N^+—CH_2—COO$;
    wherein X is an organic or inorganic anion and n is 1 or 2.

2. The composition according to claim 1, characterized in that X is selected from a chloride, a sulfate, a perchlorate, an alkyl sulfate ion, decyl sulfate, lauryl sulfate, an arylsulfonate ion, benzenesulfonate, para-toluenesulfonate, camphorsulfonate, alkylsulfonate, triflate, methanesulfonate, ethanesulfonate, decylsulfonate, laurylsulfonate, sulfosuccinate, and mixtures thereof.

3. The composition according to claim 2, wherein X is an alkylsulfonate, arylsulfonate, methanesulfonate, ethanesulfonate, triflate, para-toluenesulfonate or camphorsulfonate.

4. The composition according to claim 1, characterized in that the compounds of formulae (1), (2), (3) and (4) represent in total from 90 to 100% of the weight of the composition.

5. The composition according to claim 4, characterized in that the compounds of formulae (1), (2), (3) and (4) represent in total 100% of the weight of the composition.

6. A method of making a composition comprising combining a composition according to claim 1 with at least one ingredient chosen from plant-protection or cosmetic active agents, enzymes, chelating agents, thickeners, fatty substances, oils, waxes, pasty substances, fillers, preserving agents, pigments, dyes, antioxidants, optical brighteners, and mixtures thereof.

* * * * *

UNITED STATES PATENT AND TRADEMARK OFFICE
CERTIFICATE OF CORRECTION

PATENT NO. : 11,224,220 B2
APPLICATION NO. : 16/445441
DATED : January 18, 2022
INVENTOR(S) : Freddy Pessel et al.

It is certified that error appears in the above-identified patent and that said Letters Patent is hereby corrected as shown below:

In the Claims

Column 13,
Lines 42-43, "$X^{n\text{-}}[(CH_3)_3N^+\text{–}CH_2\text{–}CONH\text{-}R]_n$, in" should read --$X^{n\text{-}}[(CH_3)_3N^+\text{–}CH_2\text{–}CONH\text{-}R]_n$ in--.

Column 14,
Line 5, "$X^{n\text{-}}[NH_3^+R]$" should read --$X^{n\text{-}}[NH_3^+R]_n$--.
Line 11, "$X^{n\text{-}}[(CH_3)_3N^+\text{–}CH_2\text{–}COOR']n$" should read --$X^{n\text{-}}[(CH_3)_3 N^+\text{–}CH_2\text{–}COOR']_n$--.
Line 15, "$(CH_3)_3N^+\text{–}CH_2\text{–}COO$;" should read --$(CH_3)_3N^+\text{–}CH_2\text{–}COO^-$;--.

Signed and Sealed this
Eleventh Day of October, 2022

Katherine Kelly Vidal
*Director of the United States Patent and Trademark Office*